United States Patent [19]

Sams

[11] Patent Number: 5,743,889
[45] Date of Patent: Apr. 28, 1998

[54] INCREMENTING DOSAGE MECHANISM FOR SYRINGE

[76] Inventor: Bernard Sams, 22 Avondale Avenue, London, Great Britain, N12 8EJ

[21] Appl. No.: 464,839

[22] PCT Filed: Dec. 17, 1993

[86] PCT No.: PCT/GB93/02593

§ 371 Date: Jun. 7, 1995

§ 102(e) Date: Jun. 7, 1995

[87] PCT Pub. No.: WO94/15120

PCT Pub. Date: Jul. 7, 1994

[30] Foreign Application Priority Data

Dec. 18, 1992 [GB] United Kingdom ............... 9226423

[51] Int. Cl.$^6$ .................................................. A61M 5/00
[52] U.S. Cl. ........................... 604/211; 604/207; 604/218; 604/224
[58] Field of Search ........................ 604/207–211, 218, 604/224; 222/46, 48, 250, 309, 310, 325, 328

[56] References Cited

U.S. PATENT DOCUMENTS

| | | |
|---|---|---|
| 854,399 | 5/1907 | Bridge. |
| 2,250,467 | 7/1941 | Cole. |
| 3,162,217 | 12/1964 | Poli, Jr. et al.. |
| 4,498,904 | 2/1985 | Turner et al.. |
| 4,561,856 | 12/1985 | Cochran. |
| 4,592,745 | 6/1986 | Rex et al.. |
| 4,883,472 | 11/1989 | Michel. |
| 4,936,833 | 6/1990 | Sams. |
| 4,968,299 | 11/1990 | Ahlstrand et al.. |
| 4,973,318 | 11/1990 | Holm et al.. |
| 5,017,190 | 5/1991 | Simon et al.. |
| 5,042,977 | 8/1991 | Bechtold et al.. |
| 5,104,380 | 4/1992 | Holman et al.. |
| 5,112,317 | 5/1992 | Michel. |
| 5,148,067 | 9/1992 | Lasota. |
| 5,226,895 | 7/1993 | Harris ............................ 604/208 |
| 5,279,586 | 1/1994 | Balkwill ......................... 604/207 |
| 5,304,152 | 4/1994 | Sams. |

FOREIGN PATENT DOCUMENTS

| | | |
|---|---|---|
| 0498737 | 8/1992 | European Pat. Off.. |
| 3725210 | 5/1988 | Germany. |

*Primary Examiner*—Corrine M. McDermott
*Assistant Examiner*—Cris L. Rodriguez
*Attorney, Agent, or Firm*—Rader, Fishman, Grauer & McGarry

[57] ABSTRACT

A mechanism for use with a syringe to permit repeated injections of various doses has a body in which is slidably mounted a syringe piston operating rod. A plunger surrounds part of the rod and is slidably mounted in the body, a releasable screw-threaded connection being formed between the plunger and the body. An automatic one-way ball clutch interconnects the plunger and rod, and a further one-way ball clutch interconnects the body and the rod. A dose is dispensed by rotating the plunger to thread that plunger away from the further one-way clutch until a required dose is displayed through a window, the rod being held stationary by the further one-way clutch. Then, on driving the plunger forwardly, the automatic one-way ball clutch connects the plunger to the rod, so that the rod is also driven to project further from the body. Movement is limited by the forward end of the plunger by striking a cup member secured in the body.

23 Claims, 6 Drawing Sheets

INCREMENTING DOSAGE MECHANISM FOR SYRINGE

BACKGROUND OF THE INVENTION

1. Field of the Invention

This invention relates to an incrementing mechanism arranged to advance an elongate element through a pre-set distance on each cycle of operation of the mechanism. The invention in particular—but not exclusively—relates to such a mechanism adapted for use in conjunction with a hypodermic syringe, in order to assist the accurate dispensing of a predetermined dose of a medicament each time the syringe is used.

2. Description of the Prior Art

There have been many proposals for mechanisms intended for use with a hypodermic syringe, in order to ensure that an accurately metered dose is dispensed from the syringe. It is further known to provide a mechanism which allows the repeated dispensing of accurately metered, but perhaps individually variable, doses from a charged syringe. Such a mechanism is frequently used by persons who have to receive drugs or medicaments by injection on a frequent and on-going basis. For example, a diabetic may require a dose of insulin to be given by injection two or three times a day in order to maintain the blood-sugar level within an acceptable range, and a mechanism as has been described above conveniently is used with a hypodermic syringe to perform self-injection of the required dose of insulin.

In DE-A-3725210 there is disclosed a device for dispensing doses from a syringe, but the volume dispensed cannot be altered. Friction provided by an O-ring prevents a thrust rod from returning each time the mechanism is to be reset to dispense another dose, but when a spent cartridge of medicament is to be changed for a fresh cartridge, the thrust rod has to be pushed back against the friction provided by the O-ring. This mechanism lacks certainty in its operation, and if the O-ring is to provide sufficient friction to hold the thrust rod against movement during normal resetting, very considerable force will be needed to move the rod at the time of cartridge changing. Also, the O-ring can be expected to wear rapidly, so giving unreliable operation.

The known mechanisms intended for use with hypodermic syringes, to allow repeated dispensing of accurately-metered doses, tend to be somewhat complex and so are relatively expensive to manufacture. There is moreover a requirement to reduce the physical size of the mechanism as much as possible to make it convenient to carry and use as and when required, but this can reduce the reliability or the life of the mechanism. There is also a demand that such mechanisms should be simple and easy to use, in order to minimise the likelihood of erroneous operation.

SUMMARY OF THE INVENTION

It is a principal aim of the present invention to provide an incrementing mechanism suitable for use, for example, with a hypodermic syringe in order to assist the dispensing of accurately-metered doses of a drug or medicament from that syringe.

According to one aspect of the present invention, there is provided an incrementing mechanism to advance an elongate element in one direction relative to an outer tubular body within which the element is mounted, which mechanism comprises, in addition to said element and said body, a driving member slidably mounted on the body and arranged for relative turning movement with respect to the element, an end stop to limit sliding movement of the driving member in one direction, control means selectively to control movement of the driving member in the other direction dependent upon the required incremental movement of said element, automatic one-way clutch means disposed between the driving member and the element and arranged to permit relative sliding movement between the driving member and the element when the driving member is moved in said other direction but connecting the member to the element for simultaneous movement when the member is moved in said one direction, and means resisting movement of the element in said other direction, the one-way clutch means being disengaged upon relative turning movement of the driving member and element.

It will be appreciated that when the incrementing mechanism is used in conjunction with a hypodermic syringe, the mechanism allows the dispensing of an accurately metered dose from the syringe by controlling the advancement of the elongate element relative to the outer tubular body to which the syringe is connected, for each cycle of operation of the driving member. Initially, the driving member is moved in said other direction through a distance determined by the control means whilst the elongate element remains stationary under the action of said movement resisting means, but then on reversing the movement of the driving member and moving it forwardly until it engages the end stop, the elongate element is moved forwardly simultaneously, though the same distance. The actual dose dispensed is then a function of that distance moved by the elongate element and the area of the piston of the syringe or of a drug cartridge used in conjunction with the syringe and which piston is engaged by the forward end of the elongate element.

BRIEF DESCRIPTION OF THE DRAWINGS

FIGS. 1 to 6 show a first embodiment of the incrementing mechanism, FIG. 1 being a perspective view, partially cut away, of the first embodiment;

DESCRIPTION OF THE PREFERRED EMBODIMENT

In a preferred embodiment, the automatic one-way clutch means comprises first and second opposed surfaces respectively on the driving member and on the element, there being a gap between the surfaces which reduces in said other direction, and a rotational clutch member, for example in the form of a ball, constrained to lie between the surfaces. The or each ball should be constrained to overlie its associated second surface of the element notwithstanding turning movement of the driving member. Advantageously, to balance the driving force coupling the driving member to the element, the automatic one-way clutch means includes at least two diametrically-opposed pairs of surfaces together with respective associated balls, though it would be possible to provide only one, or more than two pairs of such surfaces—for example, three pairs of such surfaces equally-spaced around the elongate element.

By providing between the first surfaces of the driving member a wall which is shaped to move the ball against its spring bias, turning of the driving member relative to the element arcuately to separate said surfaces disconnects the clutch drive between the driving member and the element. Advantageously, said wall is shaped to provide in conjunction with the ball a positive click-stop position each time a first surface of the driving member overlies a second surface of the element, as the driving member is turned relative to the element.

In order to remove substantially all backlash between the driving member and the element as the member starts to move forwardly in said one direction, spring means may be arranged to drive the or each ball into its associated gap to engage both of said surfaces between which the ball lies.

In one preferred embodiment of this invention, the control means comprises thread means interconnecting the tubular body and the driving member, and a plurality of graduations on one of the driving member and tubular body and readable in conjunction with an index on the other of the driving member and the tubular body, the thread means being disengageable upon movement of the driving member at least in said one direction. The thread means may comprise internal threads within the tubular body, the driving member being a sliding fit within those threads and having at least one peg resiliently urged outwardly to engage the threads of the tubular body. Movement of the driving member in said one direction, to increment the elongate member, may then be performed by the peg riding over the threads of the tubular body. Movement of the driving member in said other direction is controlled by monitoring the graduations and index; such axial movement of the driving member may be performed by rotating the member to cause the peg to run along the internal thread of the tubular body, or by drawing the driving member in said other direction with the peg riding over the threads of the tubular member. Setting of the driving member to a position between predetermined dose settings is discouraged by virtue of the peg tending to engage in the thread form of the tubular body. Moreover, the click-stop mechanism described above assists the proper angular setting of the driving member.

In one possible arrangement, the control means comprises a sleeve threadingly engaged with the tubular body and forming an adjustable abutment to limit movement of the driving member in said other direction. There may be a plurality of graduations on one of the sleeve and the tubular body and readable in conjunction with an index on the other of the sleeve of the tubular body. In such a case, the sleeve may readily be adjustable by rotation to set a required dose.

Alternatively, the sleeve may be rotationally coupled to, but axially movable with respect to, an indicator tube which tube is also threadingly engaged with the tubular body, but by means of threads of a coarser pitch than those between the tubular body and the sleeve. By providing a plurality of graduations on one of the indicator tube and the tubular body, and readable in conjunction with an index on the other of the indicator tube and the tubular body, accurate but relatively small incremental movements of the element may be assured, with the user being able to set the position of the sleeve by monitoring the relatively large axial movement of the indicator tube.

The movement resisting means associated with the element may comprise a second automatic one-way clutch disposed between the tubular body and the element, which may be of a similar construction to said first-mentioned automatic one-way clutch, and so include spring means arranged to drive the or each clutch member into its associated gap.

The element may project from one end of the tubular body in the direction of incremental advancement of the element. That end of the body may then be adapted to be mounted on one end of a hypodermic syringe, so that the forward incremental movement of the element dispenses a measured dose from a syringe mounted on the tubular body. In this case, the mounting of the tubular body on a syringe may activate the second automatic one-way clutch, so that rearward movement of the element is thereby resisted. Conversely, removal of the syringe from the tubular member may free the second automatic one-way clutch, so permitting the element to be moved rearwardly back into the tubular body, but before this action can be completed, the first one-way clutch means must also be deactivated. In a preferred embodiment, this is achieved by turning the driving member with respect to the element so that the first and second surfaces of the clutch means no longer overlie each other. In an alternative arrangement, both the first and second one-way clutches may be simultaneously disabled by turning the elongate element with respect to the tubular body and the driving member.

By way of example only, two specific embodiments of incrementing mechanism constructed and arranged in accordance with the present invention and for use with a hypodermic syringe, will now be described in detail, reference being made to the accompanying drawings, in which:

Referring initially to FIGS. 1 to 5. it can be seen that the incrementing mechanism comprises a tubular body 10 within which is mounted a plunger 11 and a co-axial elongate syringe-operating rod 12. The forward end of the tubular body 10 is formed with a bayonet-type connector 13, to permit the connection of a syringe 14 (FIG. 2) thereto. The internal surface of the tubular body 10 has a precision moulded thread 15, for a purpose to be described below.

The plunger 11 is generally tubular and has at its rear end an enlarged head 16 fitted with an end cap 17. Slidably received within the plunger 11 is the rod 12 which also has an enlarged head 18 within the plunger 11, the head 18 being engageable with an internal shoulder 19 of the plunger 11. An automatic one-way clutch mechanism 20 serves to couple the plunger 11 to the rod 12 when the plunger is driven to the left (in FIG. 2) in the direction of arrow A, but allows the plunger 11 to be moved in the direction of arrow B whilst the rod 12 remains stationary.

Figure 2:
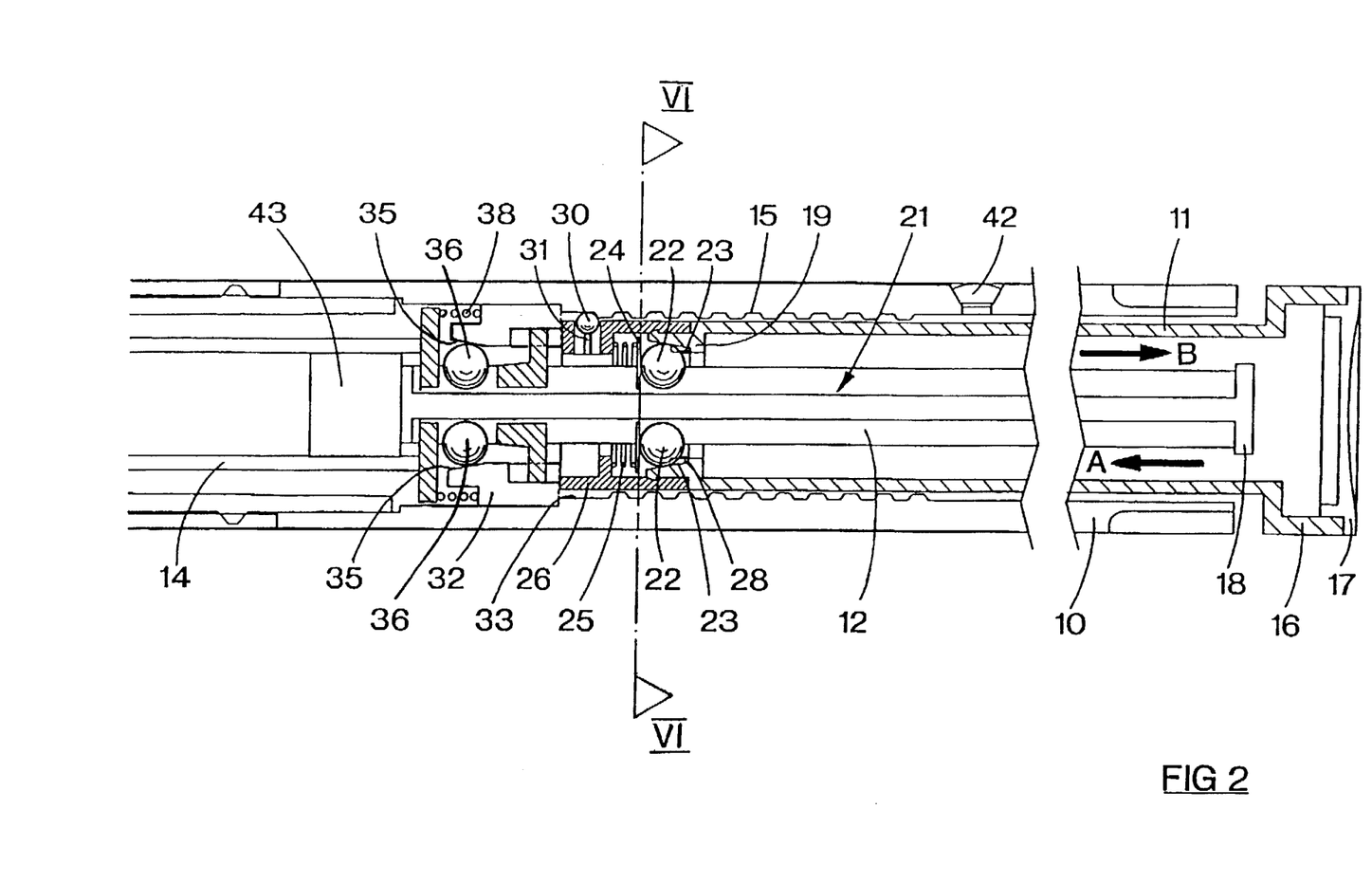
FIG. 2 is an axial section through the mechanism, when connected to a syringe.

The rod 12 has a generally H-shaped cross-section defining two channels 21, in each of which is located a respective ball 22. The plunger 11 has a pair of opposed conical surfaces 23 which may overlie the channels 21 in the rod 12, as shown in FIG. 2, whereby the balls 22 may jam between those surfaces 23 and the channels 21 of the rod 12. The balls are urged to that jamming position by a washer 24 biased by spring 25 acting against sleeve 26, connected to the forward end of the plunger 11.

Figure 3:
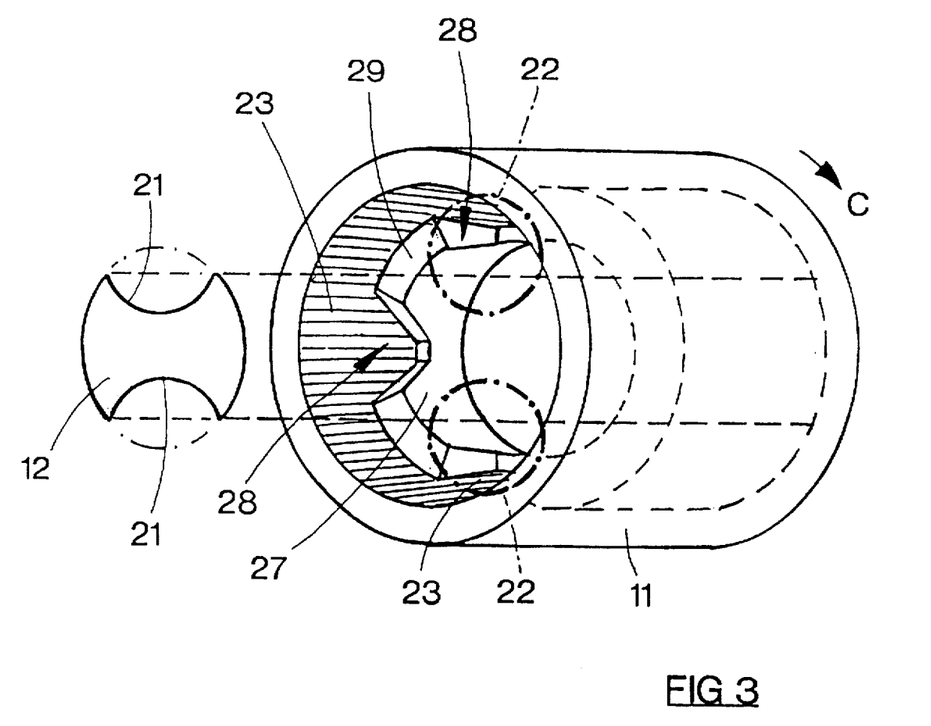
FIG. 3 is a perspective view of the front of the tubular member.
Figure 6A:
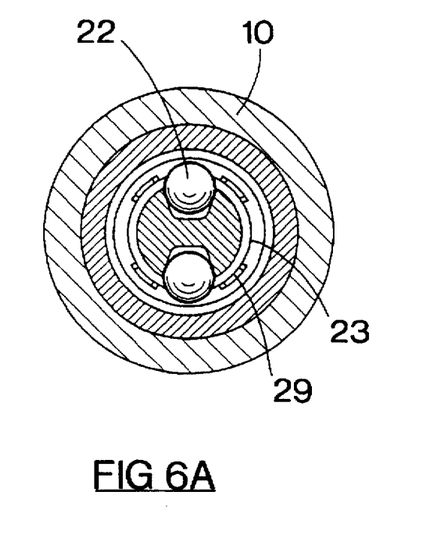
FIGS. 6A and 6B are cross-sectional views along line VI—VI marked on FIG. 2, respectively, for two different rotational settings.

Referring now to FIG. 3, the internal conical wall at the forward end of the plunger 11 is shown shaded, and it can be seen that there is a camming wall 27 which defines two opposed pairs of equi-spaced recesses 28, within which the conical wall forms the surfaces 23 against which the balls 22 may jam. When the plunger 11 is turned as shown by arrow C, the balls 22 will ride out of the recesses 28, over the end face 29 of the camming wall 27, and then back into the next pair of recesses 28, where jamming may take, place once more. Thus, when the balls are moved against the spring bias on to end faces 29 (FIG. 6B), free movement between the plunger 11 and the rod 12 is possible, though when the balls are located in the recesses 28 (FIG. 6A), the plunger may be moved in the direction of arrow B whilst the rod 12 remains stationary, but on moving the plunger 11 in the direction of arrow A, the rod 12 will be moved simultaneously therewith.

By virtue of the spring bias applied to the balls 22, a click-stop will be provided for the plunger 11 with respect to the rod 12, every quarter turn.

At the forward end of sleeve 26, a further ball 30 is located in a radial bore and is urged outwardly by a bow-shaped spring 31. The ball 30 may locate in the thread 15 formed internally within the tubular body 10, so as to impart axial movement to the plunger 11 upon the rotation thereof.

Figure 4:
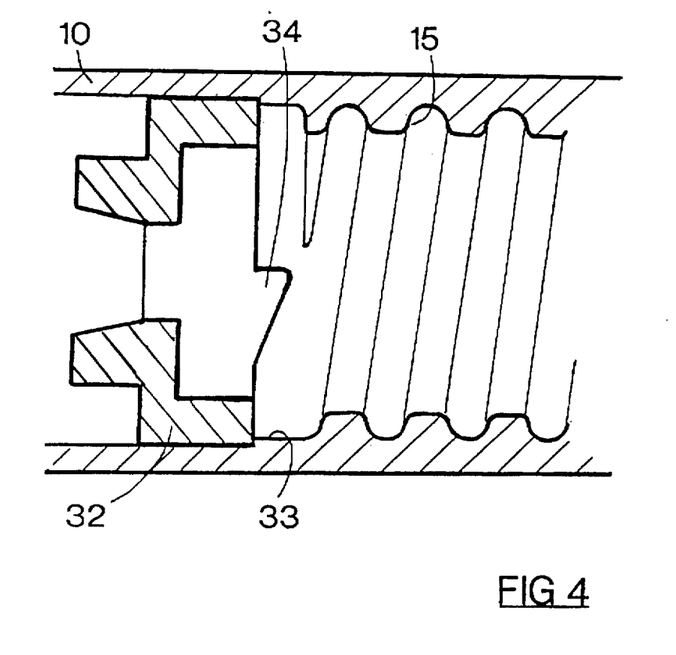
FIG. 4 is an axial section on an elongated scale of the front region of the thread within the tubular body.
Figure 5:
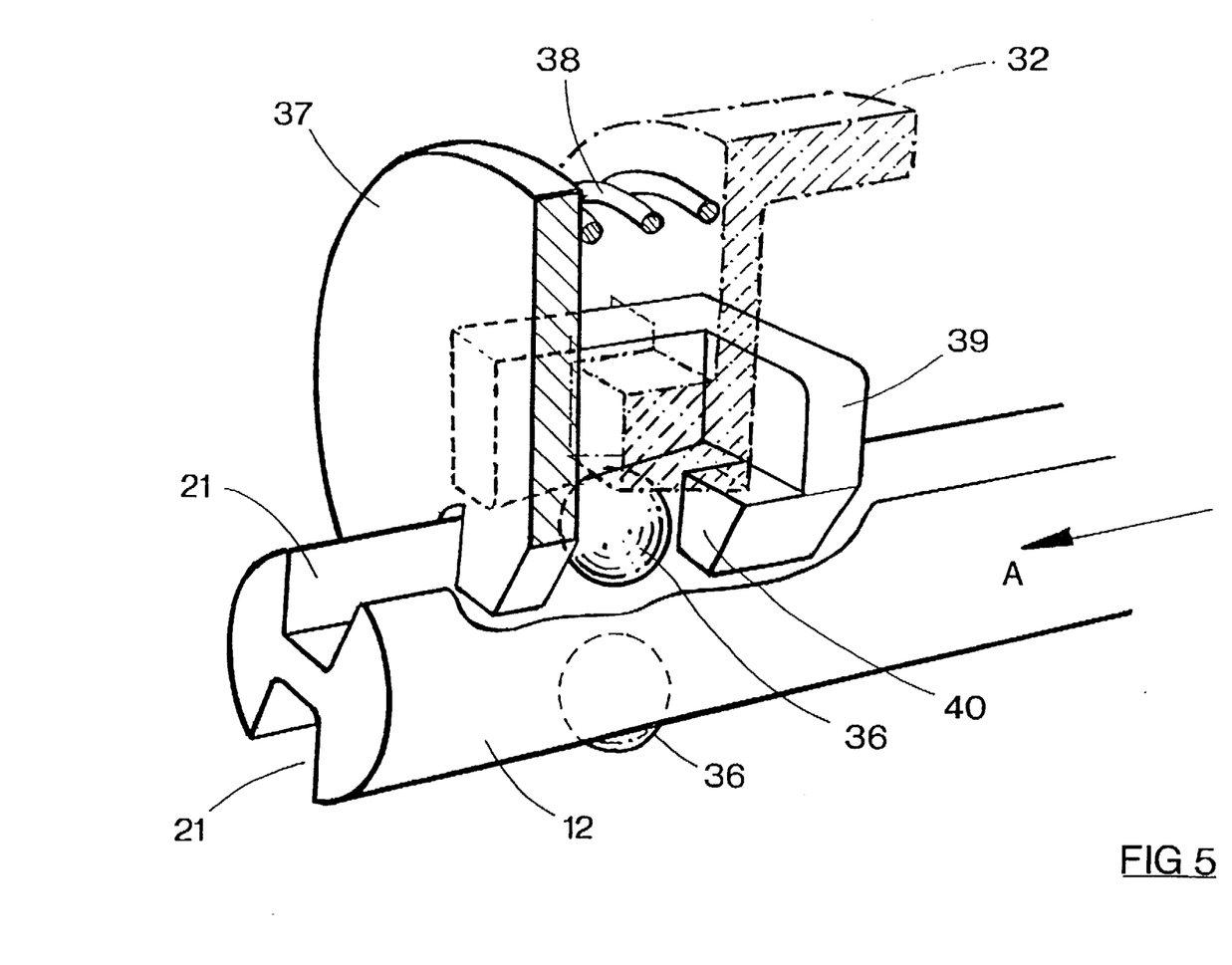
FIG. 5 is a partial view on the forward one-way clutch.

A second one-way clutch mechanism is provided at the forward end of the body 10; this includes a cup member 32 which defines at the forward end of the thread 15 an annular groove 33 (FIG. 4). The cup member has a lug 34 which serves to direct ball 30 out of the groove 33 and into the helical thread 15, upon rotation of the plunger 11 in the direction of arrow C (FIG. 3).

The cup member 32 has a central aperture through which rod 12 passes, and serves to hold the rod against rotation with respect to body 10. The member 32 further defines a pair of ramp surfaces 35 opposed to the channels 21 in the rod 12, further balls 36 being located between those ramp surfaces 35 and the rod 12 so as to form a second one-way clutch restraining movement of the rod 12 in the direction of arrow B. The balls 36 are maintained in this position by plate 37, urged to the left (in FIGS. 2 and 5) by spring 38 but held in the illustrated position by the end of a syringe 14, locked to the mechanism by the bayonet connector 13. Attached to the plate 37 is a control member 39 which passes through an opening in the cup member 32 and has a control surface 40 lying closely adjacent each ball. On removing a syringe from the body 10, the plate 37 moves to the left under the action of spring 38 and the control surfaces 40 also move to the left to prevent the balls 36 locking the rod 12 against movement, in the direction of arrow B. The control member 39 also prevents the plate 37 moving too far to the left and so releasing altogether the balls 36.

Figure 1:
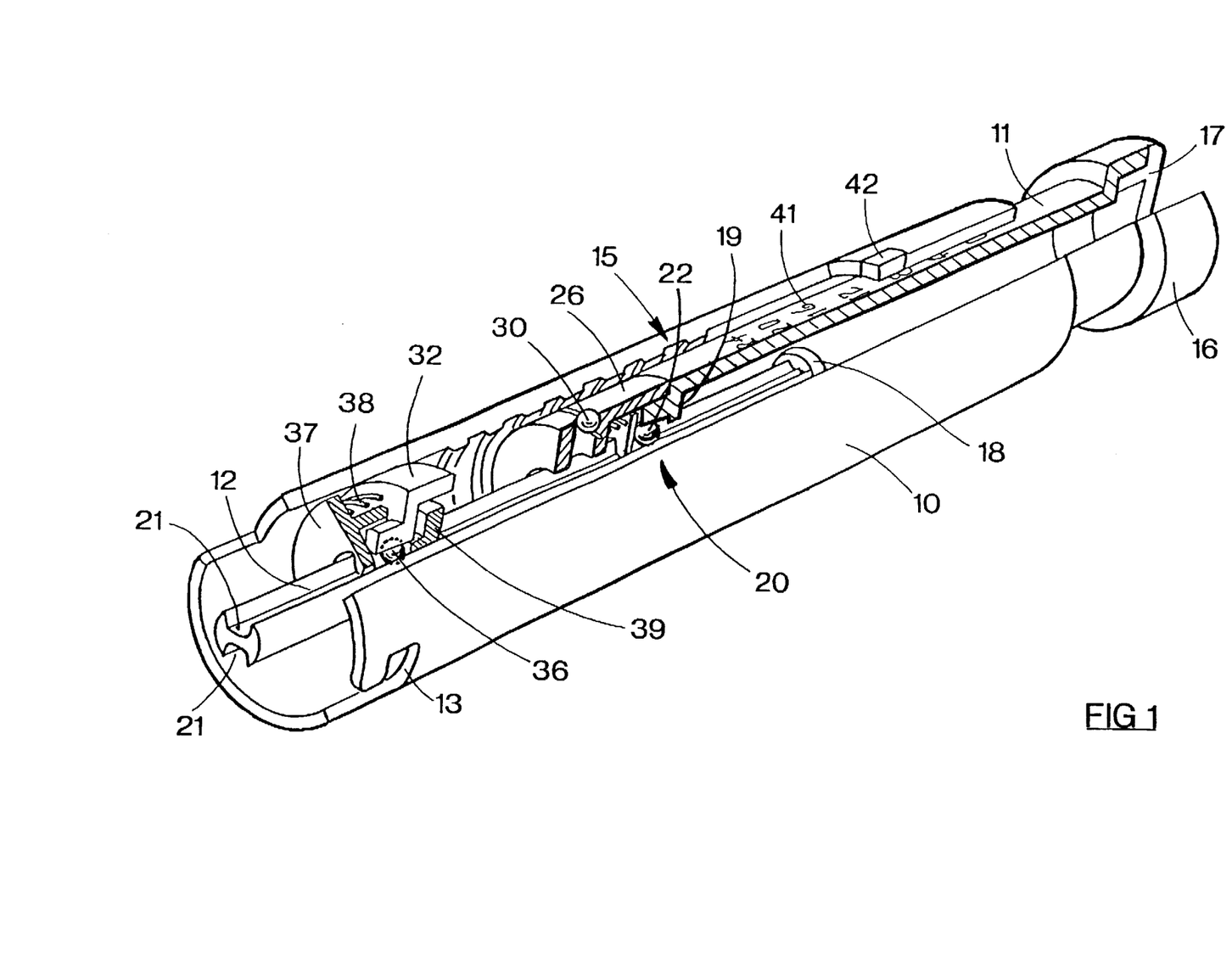

As illustrated in FIG. 1, the outer surface of the plunger 11 has a sequence of numerals 41 marked thereon, visible one at a time through a transparent window 42 provided in the tubular body 10. The numerals are provided in four axial, equi-spaced columns whereby during rotation of the plunger 11, driving the plunger in the direction of arrow B as the ball 30 runs along the thread 15, each quarter-turn the next numeral appears in the window 42. Each quarter-turn position where a numeral is visible in the window 42 is defined by the click-stop of balls 22 of the one-way clutch mechanism 20 locating in a pair of recesses 28 in the internal wall 27 of the plunger 11.

Figure 6B:
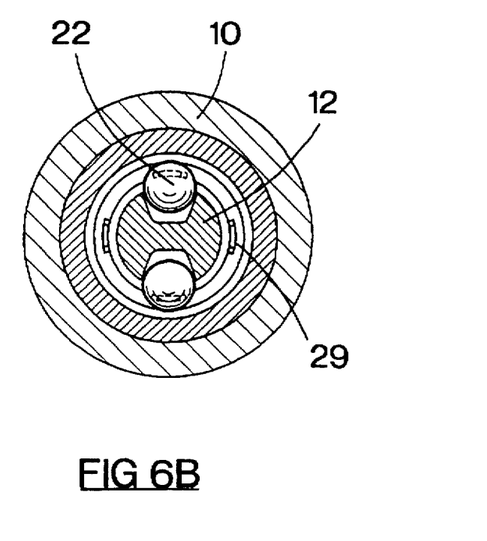

In order to use the incrementing mechanism with a syringe 14 having a piston 43, to dispense a measured dose of a medicament from that syringe, the mechanism is set to an initial position before connecting the syringe by turning the plunger 11 through one eighth of a turn to lift the balls 22 clear of the recesses 28, and so release the one-way clutch mechanism 20 (FIG. 6B). The rod 12 may then be pushed fully in the direction of arrow B, the balls 36 being prevented from locking rod 12 against movement in that direction by virtue of the control surfaces 40 being urged to the left by spring 38. The syringe 14 is then connected to the tubular body 10, so moving the balls 36 to their locking position and preventing further movement of rod 12 in the direction of arrow B.

The rod may be pushed in the direction of arrow B by the piston 43 of a new syringe, as that syringe is fitted to the mechanism. In this case, the syringe should immediately by ready for use. Otherwise, the plunger 11 is then turned in the direction of arrow C until the ball 30 picks up the thread 15 and moves the plunger 11 in the direction of arrow B to the first (smallest) dose setting. The plunger 11 is pushed in the direction of arrow A until the sleeve 26 engages the cup member 32, moving the rod 12 in the direction of arrow A. This is repeated until rod 12 engages the piston 43, whereafter the mechanism is set ready for use.

From the above position, the appropriate dose is selected either by rotating the plunger 11 in the direction of arrow C until the appropriate dose shows through window 42, or by pulling the plunger 11 in the direction of arrow B and then turning the plunger 11 until the appropriate dose is visible in the window 42. Should the required dose number be overshot, then the plunger 11 may be turned in the opposite direction, to wind the member back along the threads 15, until the appropriate numeral can be viewed; during this action, the rod 12 is not driven in the direction of arrow A, since no appreciable axial movement of the plunger 11 takes place in that direction before the balls 22 are lifted out of recesses 28 and so out of their jamming position, by internal wall 27, upon turning movement of that plunger 11. Once the dose has been set, the plunger 11 is pushed in the direction of arrow A until the forward end of the sleeve 26 engages the cup member 32, ball 30 riding over the threads 15 inside the body 10. Rod 12 is moved simultaneously with the plunger 11, to move the piston 43 in the syringe 14 and so dispense a precisely known quantity of medicament from the syringe.

The above action can be repeated until such time as the head 18 of the rod 12 engages the shoulder 19 of the plunger 11. At this point, the plunger 11 can be moved no further in the direction of arrow B and so the indicated dose is the maximum remaining amount of medicament which can be dispensed from the syringe. Once this has been discharged, the syringe (or cartridge within the syringe) must be replaced by a fresh one, following the above-described sequence of events.

Figure 7:
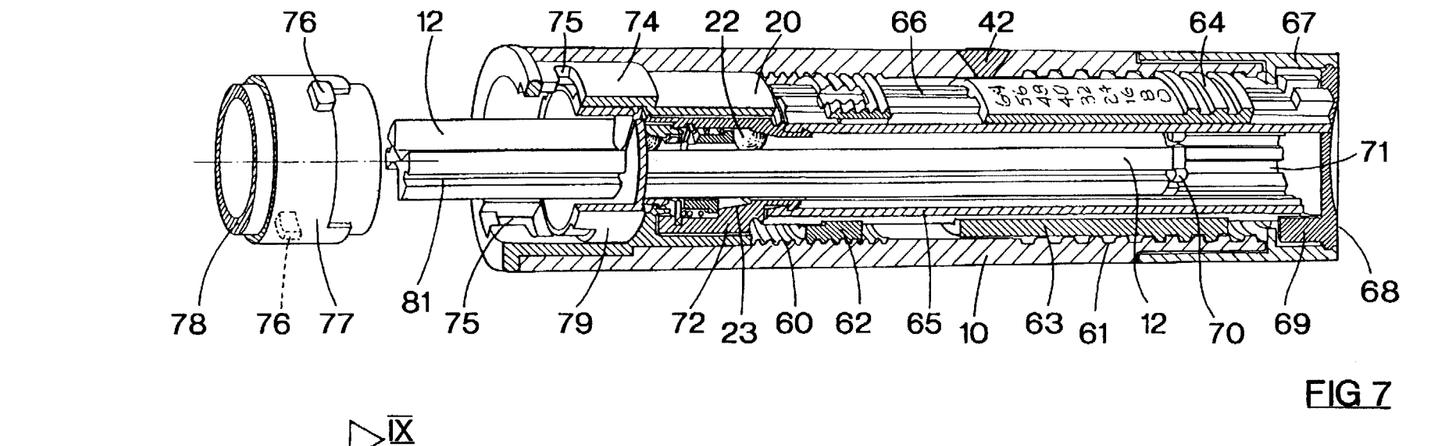
FIG. 7 is a cut-away, partial sectional view of a second embodiment of the incrementing mechanism according to the invention.
Figure 8:
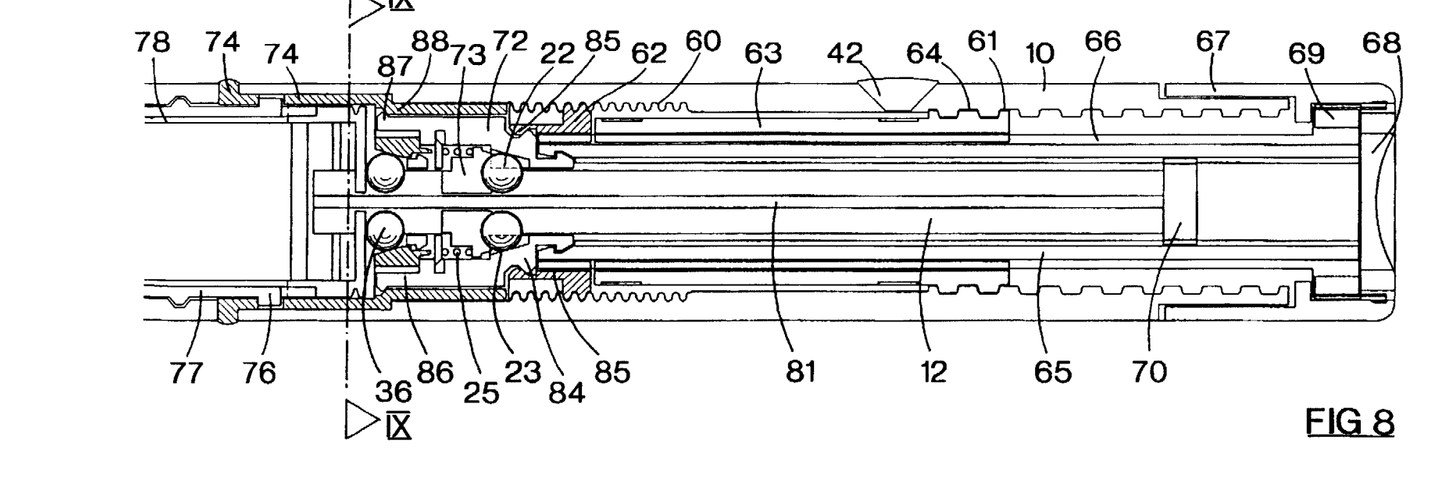
FIG. 8 is a cross-sectional view through part of the mechanism of FIG. 7.
Figure 9A:
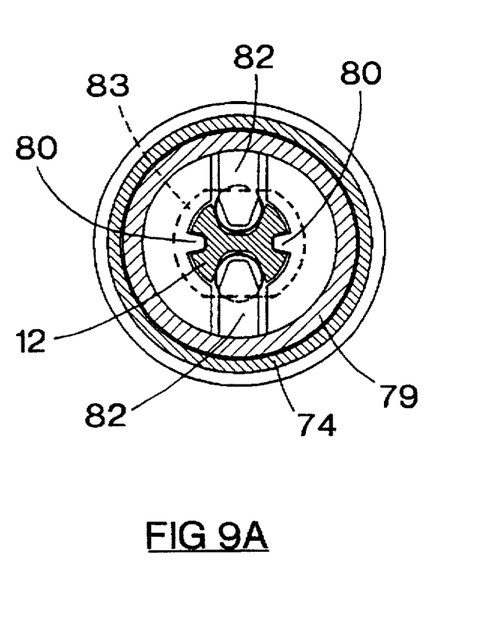
FIGS. 9 and 9B are cross-sectional views along line IX—IX of FIG. 8, respectively, for two different rotational settings.
Figure 9B:
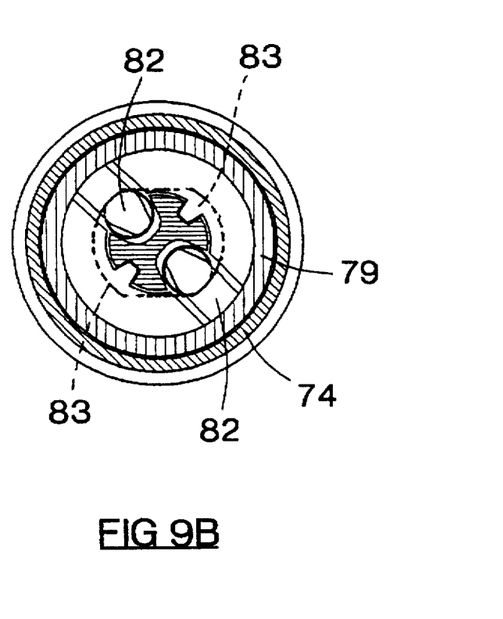

FIGS. 7 to 9 show a second embodiment of incrementing mechanism of this invention, and like parts with those of the first embodiment described above are given like reference characters; those parts will not be described in detail again here. This embodiment has been arranged to allow the accurate dispensing of relatively small doses. To permit this, two threads are formed internally in the body 10, a first thread 60 of a relatively fine pitch and a second thread 61 of a relatively coarse pitch. An externally-threaded dose control sleeve 62 is engaged with the first threads 60 and an indicator tube 63 having external threads 64 at its rear end is engaged with the second threads 61. A plunger 65 is formed with external splines 66, the sleeve 62 and tube 63 being slidably mounted on the plunger 65 by means of corresponding internal splines which prevent relative rotation therebetween. Rotation of the sleeve 62 and tube 63 is performed by turning a cap 67 rotatably mounted on the rear end of the body 10 and locked to the plunger by means of a plug 68 having legs 69 received in the splines on the plunger and in corresponding internal splines in the cap. This plug 68 could be replaced by a plug having no such legs whereby the cap may rotate freely on the body, but when the plunger is to be turned to set a different dose, a locking member may be inserted through an opening in that plug.

The rear end of the syringe operating rod 12 is provided with springy arms 70 the outer ends of which are engaged in grooves 71 formed internally in the plunger. These serve to give a 'click-stop' feel to rotation of the plunger through successive doses, and to prevent the plunger turning other than when expressly driven by cap 67.

A one-way clutch 20 is formed between rod 12 and a sleeve 72 rotatably connected to the forward end of the plunger but held against rotation with respect to the body 10; the sleeve 72 provides an internal conical surface 23 co-acting with balls 22 and has a camming wall similar to that wall 27 of the previous embodiment. Here, the balls 22 are urged rearwardly by a spring-loaded blocking member 73, rather than washer 24 (FIG. 2).

At the forward end of the body 10, there is formed a second one-way clutch to prevent rearward movement of rod 12 during rearward movement of the plunger 65. This clutch is similar to that described with reference to FIGS. 1 and 2, but is held inactive by a different mechanism, during medicament cartridge changing. A bushing 74 is mounted in the forward end of the body 10 and has bayonet slots 75 to receive dogs 76 formed externally on a cartridge holder 77, part of a cartridge being shown at 78. The rear of the cartridge holder 77 is engageable with a cap member 79 rotatably mounted within the bushing 74, so that member 79 is turned with the holder 77, during making or breaking of the bayonet connection. Cup member 79 has a pair of internal projections 80 engaged in grooves 81 formed in rod 12, so that the rod 12 will also be turned with the member 79. The member 79 further has spring fingers 82 arranged to urge balls 36 rearwardly, against a generally-conical surface formed in an internal part of bushing 74. As shown in FIGS. 9A and 9B, this conical surface is profiled to have cut-away regions 83, whereby locking is possible only when rod 12 is correctly aligned in the rotational sense with sleeve 72, as shown in FIG. 9A.

Sleeve 72 has an external rib 84 which is engageable with a groove in a forward extension 85 of the dose control sleeve 62, when the mechanism is in the initial (no dose set) position, but also when a dose has been set and the plunger 65 is then pulled fully to the right. This gives a tactile feed-back to the operator, to indicate the plunger has been pulled to the required extent. The sleeve 72 also has a plurality of forward-projecting fingers 86 each having an external rib 87, engageable with a shoulder 88 in bushing 74, when the plunger has been pushed fully to the left. In this position, the fingers project through apertures formed in the bushing 74, around the conical surface which co-acts with balls 36. Also, there is a splined connection between sleeve 72 and bushing 74, to prevent relative rotation therebetween.

This second embodiment operates in a generally similar manner to that described above with reference to FIGS. 1 to 5. A required dose is set by turning cap 67 until the appropriate numeral is visible through window 42, whereafter the plunger 65 is pulled to the right (in FIG. 7) to the limit defined by the position of dose control sleeve 62, and is then pushed to the left, to dispense the dose. The tube 63 moves axially through a relatively large extent for a given angular movement of the cap 67, so assisting the easy selection of the appropriate dose, but the sleeve 62 moves through a relatively small extent, though is accurately set axially on account of the fine threads, to allow the dispensing of a precise dose.

When a cartridge of medicament is spent, the holder 77 is released from body 10 to permit replacement of the cartridge. This action turns the rod 12 via projections 80 of the cap member 79, so moving the rod with respect to bushing 74 from the setting of FIG. 9A to that of FIG. 9B. This releases both ball clutches, so permitting the rod 12 to be moved to the right (in FIGS. 7 and 8) and allowing the installation of a fresh cartridge. The mechanism is then re-set as described above, ready for dispensing further doses.

I claim:

1. An incrementing mechanism comprising an outer tubular body having a central axis, an elongate element mounted in the outer tubular body for incremental axial movement on operation of the mechanism in one direction relative to the outer tubular body, a driving member slidably mounted in the outer tubular body for axial sliding movement in the one direction and in another direction opposite to the one direction and arranged for relative turning movement with respect to the element, an end stop connected to the outer tubular body to limit the axial sliding movement of the driving member in the one direction, control means associated with the driving member to selectively control movement of the driving member in the other direction dependent upon the required amount of incremental axial movement of said element in said one direction, automatic one-way clutch means including first and second opposed surfaces on the driving member and on the element, respectively, there being a gap between the surfaces which reduces in said other direction, the clutch means further comprising a clutch member movable in the gap between an unlocked position wherein the clutch member is disengaged from at least one of the surfaces to permit relative axial sliding movement between the driving member and the element when the driving member is moved in said other direction, and a locked position wherein the clutch member contacts both surfaces to connect the driving member to the element for simultaneous movement of the driving member and the element when the driving member is moved in said one direction, and resisting means acting on said element for resisting movement thereof in said other direction, the clutch member being disengaged from the at least one surface upon relative rotation of the driving member and element.

2. An incrementing mechanism according to claim 1, wherein the clutch member comprises a ball.

3. An incrementing mechanism according to claim 1, wherein said first surface on the driving member includes at least two channel-shaped diametrically-opposed surfaces on the driving member and the second surface on the element comprises at least two surfaces on the element facing the first surfaces to thereby form a pair of diametrically opposing gaps, and further wherein the clutch member comprises a ball in each gap.

4. An incrementing mechanism according to claim 3, wherein spring means acts on said balls to drive each ball generally in the other direction and normally into its associated gap to inter-engage said surfaces between which each ball lies.

5. An incrementing mechanism according to claim 4 wherein each ball is constrained to overlie its associated second surface of the element, and between the first surfaces of the driving member there is defined a wall which is shaped to move each ball against its spring bias to disconnect the clutch drive between the driving member and the element upon rotation of the driving member relative to the element.

6. An incrementing mechanism according to claim 1 wherein the control means comprises a thread means interconnecting the tubular body and the driving member, and a plurality of graduations on one of the driving member and tubular body and readable in conjunction with an index on the other of the driving member and the tubular body, the thread means being disengageable upon movement of the driving member at least in said one direction.

7. An incrementing mechanism according to claim 6 wherein said graduations are marked on the external surface of the driving member and are visible one at a time through a window formed in the tubular body.

8. An incrementing mechanism according to claim 1 wherein the control means comprises a sleeve threadingly engaged with the tubular body and forming an adjustable abutment to limit movement of the driving member in said other direction.

9. An incrementing mechanism according to claim 8, wherein there is a plurality of graduations on one of the sleeve and tubular body and readable in conjunction with an index (42) on the other of the sleeve and the tubular body.

10. An incrementing mechanism according to claim 9, wherein both the sleeve and indicator tube are slidably but non-rotatably mounted on the driving member, which driving member is rotatable to effect control of the incremental movement of the elongate element.

11. An incrementing mechanism according to claim 1 wherein said resisting means comprises a second automatic one-way clutch disposed between the tubular body and the element.

12. The combination of an incrementing mechanism according to claim 1 and further comprising a hypodermic syringe including a piston slidable within a cylinder to dispense liquid charged in the cylinder, the piston being coupled to the elongate element to move with the elongate element as the driving member is moved in said one direction, towards the piston, thereby to dispense liquid.

13. An incrementing mechanism comprising an outer tubular body having a central axis, an elongate element mounted in the outer tubular body for incremental axial movement on operation of the mechanism in one direction relative to the outer tubular body, a driving member slidably mounted in the outer tubular body for axial sliding movement in the one direction and in another direction opposite to the one direction and arranged for relative turning movement with respect to the element, an end stop connected to the outer tubular body to limit the axial sliding movement of the driving member in the one direction, control means associated with the driving member to selectively control movement of the driving member in the other direction dependent upon the required amount of incremental axial movement of said element in said one direction, said control means comprising a thread means interconnecting the tubular body and the driving member and a plurality of graduations on one of the driving member and tubular body and readable in conjunction with an index on the other of the driving member and the tubular body, the thread means being disengageable upon movement of the driving member at least in said one direction, automatic one-way clutch means disposed between the driving member and the element and arranged to permit relative axial sliding movement between the driving member and the element when the driving member is moved in said other direction, and connecting the driving member to the element for simultaneous movement of the driving member and the element when the driving member is moved in said one direction, and resisting means acting on said element for resisting movement thereof in said other direction, the one-way clutch means being disengaged upon rotation of the driving member and element, and further wherein the outer tubular body is internally threaded, the driving member is a sliding fit within the threads of the outer tubular body, and the driving member has at least one peg resiliently urged outwardly to engage the threads of the outer tubular body.

14. An incrementing mechanism comprising an outer tubular body having a central axis, an elongate element mounted in the outer tubular body for incremental axial movement on operation of the mechanism in one direction relative to the outer tubular body, a driving member slidably mounted in the outer tubular body for axial sliding movement in the one direction and in another direction opposite to the one direction and arranged for relative turning movement with respect to the element, an end stop connected to the outer tubular body to limit the axial sliding movement of the driving member in the one direction, control means associated with the driving member to selectively control movement of the driving member in the other direction dependent upon the required amount of incremental axial movement of said element in said one direction, a first automatic one-way clutch means disposed between the driving member and the element and arranged to permit relative axial sliding movement between the driving member and the element when the driving member is moved in said other direction, and connecting the driving member to the element for simultaneous movement of the driving member and the element when the driving member is moved in said one direction, the first one-way clutch means being disengaged upon rotation of the driving member and element, and further comprising a second automatic one-way clutch disposed between the tubular body and the element, the second one-way clutch comprising first and second opposed surfaces on the tubular body and on the element, respectively, there being a gap between the surfaces which reduces in said other direction, and a clutch member constrained to lie between the surfaces.

15. An incrementing mechanism according to claim 14, wherein spring means acts on the clutch member to drive the clutch member into its associated gap to engage both of said surfaces between which the clutch member lies.

16. An incrementing mechanism according to claim 14, wherein the element projects from one end of the outer tubular body in the direction of incremental advancement of the element, and the one end of the outer tubular body is adapted to be mounted on one end of a hypodermic syringe so that the forward incremental movement of the element may dispense a measured dose from a mounted syringe.

17. An incrementing mechanism according to claim 16, wherein spring means are arranged to drive the clutch member into its associated gap to engage both of said surfaces between which the clutch member lies, and the mounting of the tubular body on a syringe charges the spring means for the second automatic one-way clutch.

18. An incrementing mechanism comprising an outer tubular body, an elongate element mounted within the outer tubular body for advancement on operation of the mechanism in one direction relative to the outer tubular body, a driving member slidably mounted on the outer tubular body and arranged for relative turning movement with respect to the element, an end stop connected to the outer tubular body to limit sliding movement of the driving member in one direction, control means associated with the driving member selectively to control movement of the driving member in the other direction dependent upon the required incremental movement of said element, automatic one-way clutch means disposed between the driving member and the element and arranged to permit relative sliding movement between the driving member and the element when the driving member is moved in said other direction but connecting the driving member to the element for simultaneous movement when the driving member is moved in said one direction, and resisting means acting on said element for resisting movement thereof in said other direction, the one-way clutch means being disengaged upon relative turning movement of the driving member and element and comprising first and second opposed surfaces, respectively, on the driving member and on the element, there being a gap between the surfaces which reduces in said other direction, a ball constrained to lie between the surfaces and to overlie the second surface, spring means acting on said ball to drive the ball into said gap to inter-engage said first and second opposed surfaces, and there is defined a wall on the driving member which said wall is shaped to move the ball against the spring means to disconnect the clutch drive between the driving member and the element upon turning the driving member relative to the element.

19. An incrementing mechanism comprising an outer tubular body, an elongate element mounted within the outer tubular body for advancement on operation of the mechanism in one direction relative to the outer tubular body, a driving member slidably mounted on the outer tubular body and arranged for relative turning movement with respect to the element, an end stop connected to the outer tubular body to limit sliding movement of the driving member in one direction, control means associated with the driving member selectively to control movement of the driving member in the other direction dependent upon the required incremental movement of said element, automatic one-way clutch means disposed between the driving member and the element and arranged to permit relative sliding movement between the driving member and the element when the driving member is moved in said other direction but connecting the driving member to the element for simultaneous movement when the driving member is moved in said one direction, and resisting means acting on said element for resisting movement thereof in said other direction, the one-way clutch means being disengaged upon relative turning movement of the driving member and element and comprising at least two pairs of channel-shaped first and second opposed surfaces, respectively, on the driving member and on the element, there being a gap between each pair of surfaces which reduces in said other direction, a ball associated with each pair of surfaces and constrained to lie therebetween and overlie the second surface, spring means acting on each said ball to drive the ball into said gap to inter-engage said first and second opposed surfaces, and there is defined a wall on the driving member which said wall is shaped to move each ball against the spring means to disconnect the clutch drive between the driving member and the element upon turning the driving member relative to the element.

20. An incrementing mechanism comprising an outer tubular body, an elongate element mounted within the outer tubular body for advancement on operation of the mechanism in one direction relative to the outer tubular body, a driving member slidably mounted on the outer tubular body and arranged for relative turning movement with respect to the element, an end stop connected to the outer tubular body to limit sliding movement of the driving member in one direction, control means associated with the driving member selectively to control movement of the driving member in the other direction dependent upon the required incremental movement of said element, automatic one-way clutch means disposed between the driving member and the element and arranged to permit relative sliding movement between the driving member and the element when the driving member is moved in said other direction but connecting the driving member to the element for simultaneous movement when the driving member is moved in said one direction, the one-way clutch means being disengaged upon relative turning movement of the driving member and element, and a second one-way clutch disposed between the outer tubular body and the element to resist movement of said element in said other direction, which second one-way clutch comprises first and second opposed surfaces respectively on the outer tubular body and on the element, there being a gap between the surfaces which reduces in said other direction, and a rotational clutch member constrained to lie between the surfaces.

21. An incrementing mechanism according to claim 20, wherein spring means acts on said rotational clutch member of the second one-way clutch, to drive said clutch member into its associated gap to engage both of said further surfaces between which the rotational clutch member lies.

22. An incrementing mechanism comprising an outer tubular body, an elongate element mounted within the outer tubular body for advancement on operation of the mechanism in one direction relative to the outer tubular body, the element projecting from one end of the outer tubular body in the direction of incremental advancement of the element, a driving member slidably mounted on the outer tubular body and arranged for relative turning movement with respect to the element, an end stop connected to the outer tubular body to limit sliding movement of the driving member in one direction, control means associated with the driving member selectively to control movement of the driving member in the other direction dependent upon the required incremental movement of said element, automatic one-way clutch means disposed between the driving member and the element and arranged to permit relative sliding movement between the driving member and the element when the driving member is moved in said other direction but connecting the driving member to the element for simultaneous movement when the driving member is moved in said one direction, the one-way clutch means being disengaged upon relative turning movement of the driving member and element, resisting means acting on said element for resisting movement thereof in said other direction, and spring means acting on the resisting means to urge the resisting means to an engaged setting, said one end of the outer tubular body is adapted to be mounted on one end of a hypodermic syringe so that the forward incremental movement of the element may dispense a measured dose from a mounted syringe, and the mounting of the outer tubular body on a syringe charges said spring means for the resisting means.

23. An incrementing mechanism comprising an outer tubular body having a central axis, an elongate element mounted in the outer tubular body for incremental axial movement in one axial direction relative to the outer tubular body on operation of the mechanism, a driving member slidably mounted in the outer tubular body for axial sliding movement in the one axial direction and in another axial direction opposite to the one axial direction and arranged for rotation with respect to the element, an end stop connected to the outer tubular body to limit the axial sliding movement of the driving member in the one direction, a control mechanism operably associated with the driving member to selectively adjust the range of movement of the driving member in the other axial direction dependent upon a required amount of incremental axial movement of said element in said one axial direction, an automatic one-way clutch including a clutch member operatively associated with the driving member and the element, the clutch member being displaceable to a first position to couple the driving member to the element when the driving member is moved in the one axial direction to thereby simultaneously move the driving member and the element in the one axial direction, the clutch member being displaceable to a second position when the driving member is moved in said other axial direction to decouple the driving member from the element and permit axial sliding movement of the driving member in the other axial direction with respect to the element.

* * * * *